United States Patent
Ogura

(10) Patent No.: US 9,314,158 B2
(45) Date of Patent: Apr. 19, 2016

(54) OPHTHALMOLOGIC APPARATUS, CONTROL METHOD

(71) Applicant: CANON KABUSHIKI KAISHA, Tokyo (JP)

(72) Inventor: Hiraku Ogura, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 134 days.

(21) Appl. No.: 14/075,922

(22) Filed: Nov. 8, 2013

(65) Prior Publication Data

US 2014/0132930 A1    May 15, 2014

(30) Foreign Application Priority Data

Nov. 9, 2012    (JP) ................. 2012-247356

(51) Int. Cl.
*A61B 3/10* (2006.01)
*A61B 3/00* (2006.01)
*A61B 3/12* (2006.01)
*A61B 3/14* (2006.01)

(52) U.S. Cl.
CPC ... *A61B 3/12* (2013.01); *A61B 3/14* (2013.01); *A61B 3/102* (2013.01)

(58) Field of Classification Search
USPC ......................... 351/211, 216, 246
See application file for complete search history.

(56) References Cited

U.S. PATENT DOCUMENTS

| 8,157,377 | B2 | 4/2012 | Takai et al. | |
|---|---|---|---|---|
| 2009/0244483 | A1* | 10/2009 | Yoshino et al. | 351/206 |
| 2011/0292339 | A1 | 12/2011 | Itoh | |
| 2012/0050677 | A1 | 3/2012 | Ohban | |

FOREIGN PATENT DOCUMENTS

| CN | 1951314 A | 4/2007 |
|---|---|---|
| CN | 101574256 A | 11/2009 |
| EP | 1752084 A2 | 2/2007 |
| EP | 2106741 A1 | 10/2009 |
| JP | 2009268772 A | 11/2009 |
| JP | 4744973 B2 | 8/2011 |

\* cited by examiner

*Primary Examiner* — Jack Dinh
(74) *Attorney, Agent, or Firm* — Canon USA Inc. IP Division

(57) ABSTRACT

An ophthalmologic apparatus includes a focusing lens provided in an optical path connecting a subject's eye and an imaging unit, a diopter correction lens provided in the optical path to be insertable and removable, and a position determination unit configured to determine a position of the focusing lens on the optical path in a state where the diopter correction lens is inserted, based on an in-focus state where the diopter correction lens is not inserted.

16 Claims, 7 Drawing Sheets

OPHTHALMOLOGIC APPARATUS, CONTROL METHOD

BACKGROUND OF THE INVENTION

1. Field of the Invention

The present invention relates to an ophthalmologic apparatus, a control method, and a program.

2. Description of the Related Art

Japanese Patent Application Laid-Open No. 2009-268772 discusses automatic focusing system using a positional relationship between two focus index images obtained by return light of divided focus indexes projected onto a fundus of a subject's eye.

If a subject's eye is highly myopic (near-sighted) or highly hyperopic (far-sighted), it is known that a diopter correction lens is inserted into an observation imaging optical system. When the diopter correction lens is inserted, an optical characteristic of the observation imaging optical system changes, and an optical relationship between a focus index projection unit and the observation imaging optical system changes. Therefore, focus detection using above-described focus index images becomes difficult.

On the other hand, Japanese Patent No. 4744973 discusses an ophthalmologic imaging apparatus capable of performing automatic focusing even after a diopter correction lens is inserted using a focus detection method utilizing a contrast of a focus index or the like.

However, a period of time required to perform focus detection based on the contrast becomes longer than that when focus indexes are used, until focusing is completed, because the focus detection based on the contrast has to search for a position where an evaluation value becomes a peak while driving a focusing lens.

SUMMARY OF THE INVENTION

The present invention is directed to an ophthalmologic apparatus and a method capable of preventing, if a diopter correction lens needs to be inserted, a period of time required to complete focusing from being lengthened.

The present invention is not limited thereto. It is one of other objects of the present invention to produce a function and effect introduced by each configuration illustrated in an exemplary embodiment for implementing the invention, described below, and not obtained by a conventional technique.

According to an aspect of the present invention, an ophthalmologic apparatus includes a focusing lens provided in an optical path connecting a subject's eye and an imaging unit, a diopter correction lens provided in the optical path to be insertable and removable, and a position determination unit configured to determine a position on the optical path of the focusing lens while the diopter correction lens is inserted based on an in-focus state where the diopter correction lens is not inserted.

Further features of the present invention will become apparent from the following description of exemplary embodiments with reference to the attached drawings.

DESCRIPTION OF THE EMBODIMENTS

An exemplary embodiment of the present invention will be described in detail below with reference to the drawings.

The exemplary embodiment of the present invention will be described in detail below with reference to FIGS. 1 to 6A, 6B, 6C, and 6D.

Figure 1:
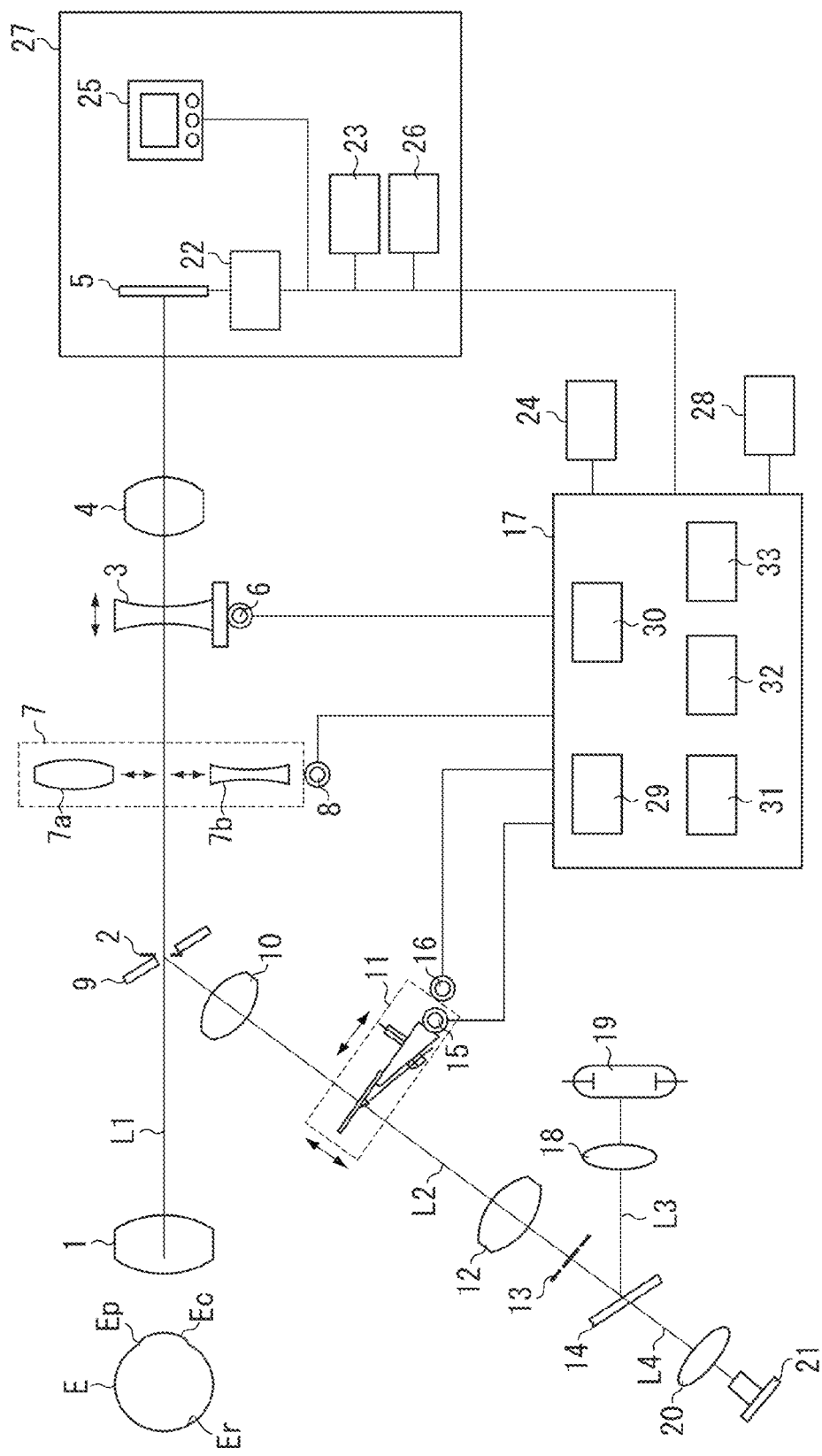
FIG. 1 illustrates an example of a configuration of an ophthalmologic apparatus according to an exemplary embodiment.

FIG. 1 illustrates an example of a configuration of a fundus camera (i.e., ophthalmologic apparatus). An objective lens 1 is arranged opposite to a subject's eye E, and an imaging diaphragm 2, a focusing lens 3, an imaging lens 4, and an image sensor 5 having sensitivity to visible light and infrared light, for example, are provided on its optical axis L1.

The focusing lens 3 is connected to a focusing lens driving unit 6, and moves in a direction of the optical axis L1. More specifically, the focusing lens 3 corresponds to an example of a focusing lens provided in an optical path connecting the subject's eye E and an imaging unit.

A diopter correction unit 7 is provided between the imaging diaphragm 2 and the focusing lens 3 and connected to a diopter correction lens driving unit 8. The diopter correction unit 7 includes a convex lens 7a (a diopter correction lens for hyperopia) and a concave lens 7b (a diopter correction lens for miopia) insertable onto and removable from the optical axis L1 so as to perform focusing on a fundus Er of a highly myopic or highly hyperopic subject's eye E, on which only the focusing lens 3 is not enough to perform focusing. The diopter correction unit 7 can change a diopter range in which focusing can be performed by inserting and removing the lenses 7a and 7b onto and from the optical axis L1. The diopter correction unit 7 corresponds to an example of a diopter correction lens provided to be insertable onto and removable from the optical path connecting the subject's eye E and the imaging unit. The convex lens 7a or the concave lens 7b may be merely referred to as a diopter correction lens.

An optical system leading to the imaging lens 4 from the objective lens 1 constitutes an observation imaging optical system. The observation imaging optical system, together with the image sensor 5, constitutes a fundus image observation imaging unit.

On the other hand, a perforated mirror 9 is obliquely disposed in the vicinity of the imaging diaphragm 2. A lens 10, a focus index projection unit 11, a lens 12, a ring diaphragm 13, and a dichroic mirror 14 are arranged on an optical axis L2 in a reflection direction of the perforated mirror 9.

Figure 2:
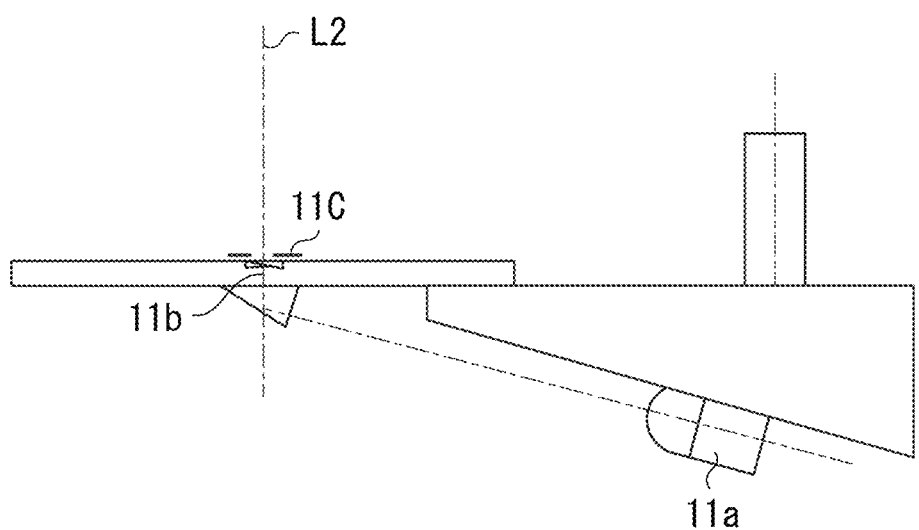
FIG. 2 illustrates an example of a configuration of a focus index projection unit.

As illustrated in FIG. 2, the focus index projection unit 11 includes a light emitting diode (LED) 11a for projecting indexes, a prism 11b for dividing a light source, and a focus index mask 11c forming an outer shape of a focus index. More specifically, the focus index projection unit 11 corresponds to an example of a projection unit for projecting divided indexes onto the subject's eye E. The projection device of the indexes are not limited to the LED 11a. Another light source may be used.

The focus index projection unit 11 includes a focus index shift driving unit 15, which moves on the optical axis L2, and a focus index insertion/removal driving unit 16 for inserting and removing the focus index projection unit 11 onto and from the optical axis L2.

The focus index projection unit 11 can be inserted onto the optical axis L2 and driven to be shifted on the optical axis L2 during fundus observation in response to control performed by a system control unit 17, and is retracted from the optical axis L2 so that the focus indexes are not taken in a captured image during imaging.

The ring diaphragm 13 includes a ring-shaped opening arranged at a position optically substantially conjugate with a pupil Ep of the subject's eye E by the objective lens 1 and the lenses 10 and 12, and including a light shielding portion at the center of the optical axis L2. The dichroic mirror 14 has a property of transmitting infrared light and reflecting visible light, for example.

A condenser lens 18 and a flash light source 19 serving as an imaging light source for emitting visible pulse light are arranged on an optical axis L3 in a reflection direction of the dichroic mirror 14. A condenser lens 20 and an infrared LED 21 serving as an observation light source having a plurality of infrared LEDs for emitting infrared stationary light, for example, are arranged on an optical axis L4 in a transmission direction of the dichroic mirror 14. An optical system leading to the condenser lens 20 from the objective lens 1 constitutes a fundus illumination optical system. The fundus illumination optical system and the flash light source 19 serving as an imaging light source constitute an imaging light illumination unit, and the fundus illumination optical system and the infrared LED 21 serving as an observation light source constitute an observation light illumination unit.

In the present exemplary embodiment, the flash light source 19 is a broadband wavelength light source for emitting light having a wavelength of 420 to 750 nm, for example, and the infrared LED 21 is a single wavelength light source for emitting light having a wavelength of 850 nm, for example. The respective wavelengths of the flash light source 19 and the infrared LED 21 are not limited to the above-mentioned values, and may be other values, respectively.

The fundus image observation imaging unit, the imaging light illumination unit, and the observation light illumination unit are retained in one housing, for example, to constitute a fundus camera optical unit. The fundus camera optical unit is laid on a slide base (not illustrated), and can be aligned with the subject's eye E.

An output of the image sensor 5 is converted into a digital signal by an analog-to-digital (A/D) conversion element 22, and is stored in a memory 23. Further, the output of the image sensor 5, which has been converted into the digital signal, is connected to the system control unit 17 that controls the entire apparatus. The system control unit 17 includes a processing device such as a central processing unit (CPU). An image memory 24 is connected to the system control unit 17, and stores still images, which have been captured by the image sensor 5, as a digital image.

Further, the system control unit 17 is connected to the focusing lens driving unit 6, the diopter correction lens driving unit 8, the focus index shift driving unit 15, the focus index insertion/removal driving unit 16, and an operation input unit 28. The system control unit 17 also includes an in-focus state detection unit 29, a movement amount calculation unit 30, a diopter correction determination unit 31, an in-focus position determination unit 32, and a driving control unit 33.

The in-focus state detection unit 29 detects an in-focus state on the subject's eye E based on a position of the focusing lens 3 and image information obtained from the image sensor 5. An amount of shift between focus index images 33a and 33b to be detected by the in-focus state detection unit 29 is a concept including a signal representing the shift amount of the focus index images 33a and 33b, and is not limited to the amount of shift itself.

If the position of the focusing lens 3 is a predetermined position such as an initial position (e.g., a position of 0 diopter) when the focusing lens 3 detects the in-focus state, the in-focus state detection unit 29 can also detect the in-focus state from the amount of shift between the focus index images 33a and 33b. If the amount of shift between the focus index images 33a and 33b is represented as an absolute value, the in-focus state detection unit 29 further detects the in-focus state using a positional relationship between the focus index images 33a and 33b. Whether the position of the focusing lens 3 is used and whether the positional relationship between the focus index images 33a and 33b is used are similar for the other constituent elements of the system control unit 17.

The movement amount calculation unit 30 calculates an amount of movement (an amount of driving) of the focusing lens 3 to complete focusing based on the focus state detected by the in-focus state detection unit 29. More specifically, the amount of movement of the focusing lens 3 is calculated so that the shift between the focus index images 33a and 33b is eliminated. The movement amount calculation unit 30 refers to a table, in which the amount of movement of the focusing lens 3 and the amount of shift between the focus index images 33a and 33b are associated with each other, stored in a memory or the like, for example, to calculate an amount of movement required to complete the focusing of the focusing lens 3. More specifically, the movement amount calculation unit 30 calculates the amount of driving of the focusing lens 3, which is required for the focusing, based on an in-focus state where a diopter correction lens is not inserted.

The diopter correction determination unit 31 determines whether the diopter correction lens is inserted into or retracted from the observation imaging optical system based on positions of a switch in the operation input unit 28 and the focusing lens 3 and the focus state detected by the in-focus state detection unit 29, for example. More specifically, the diopter correction determination unit 31 detects the position of the focusing lens 3, and determines whether the focusing lens 3 is beyond its movable range if it is moved by the amount of movement, which has been calculated by the movement amount calculation unit 30, from the detected position thereof. The diopter correction determination unit 31 determines that the diopter correction lens needs to be inserted if the focusing lens 3 is beyond the movable range while determining that the diopter correction lens need not be inserted if the focusing lens 3 is within the movable range. More specifically, the diopter correction determination unit 31 corresponds to an example of a determination unit for determining whether the diopter correction lens is inserted into the optical path based on the focus state where the diopter correction lens is not inserted. More specifically, the diopter correction determination unit 31 serving as an example of the determination unit acquires the amount of driving of the focusing lens 3, which is required for the focusing, based on the focus state where the diopter correction lens is not inserted, and inserts the diopter correction lens into the optical path if the focusing lens 3 is beyond the movable range when driven by the amount of driving.

The in-focus position determination unit 32 determines an in-focus position. More specifically, the in-focus position determination unit 32 determines the in-focus position in a state where the diopter correction lens is inserted.

First, the in-focus position determination unit 32 calculates the diopter of the subject's eye E from the amount of shift between the focus index images 33a and 33b and the position of the focusing lens 3, for example, in a state where the diopter correction lens is not inserted into the optical path. A difference between the diopter of the subject's eye E and power of the diopter correction lens is calculated. The difference represents a diopter that cannot be corrected by the diopter correction lens. The in-focus position determination unit 32 determines a position, corresponding to the difference, on the optical path of the focusing lens 3 as the in-focus position. The memory stores a table in which the diopter and the position of the focusing lens 3 are associated with each other, for example. The in-focus position determination unit 32 refers to the stored table, for example, to determine the position of the focusing lens 3, corresponding to the difference, on the optical path thereof. More specifically, the in-focus position determination unit 32 corresponds to an example of a position determination unit for determining the position of the focusing lens 3 on the optical path in a state where the diopter correction lens is inserted, based on the in-focus state where the diopter correction lens is not inserted (or the in-focus state and the position of the focusing lens 3 on the optical path). More specifically, the in-focus position determination unit 32 serving as an example of the position determination unit determines the position of the focusing lens 3 on the optical path in a state where the diopter correction lens is inserted, based on the in-focus state where the diopter correction lens is not inserted, which is obtained from a plurality of target images (an amount of shift between the plurality of index images).

Timing at which the in-focus position determination unit 32 determines the in-focus position is a timing when the diopter correction determination unit 31 determines that the diopter correction lens is inserted into the optical path. More specifically, if the determination unit determines that the diopter correction lens is to be inserted, the position determination unit determines the position of the focusing lens 3 on the optical path thereof. However, the timing at which the in-focus position determination unit 32 determines the in-focus position may be a timing before the determination by the diopter correction determination unit 31.

If the position of the focusing lens 3 is the predetermined position such as the initial position when processing for determining the in-focus position is performed, the in-focus position determination unit 32 may calculate the diopter of the subject's eye E from the amount of shift between the focus index images 33a and 33b (see FIG. 4).

The driving control unit 33 drives the focusing lens 3 and the diopter correction lens. The driving control unit 33 drives the focusing lens 3 via the focusing lens driving unit 6 to the in-focus position determined by the in-focus position determination unit 32. More specifically, the driving control unit 33 moves the focusing lens 3 to the in-focus position. That is, the driving control unit 33 corresponds to an example of a driving unit for driving the focusing lens 3.

The driving control unit 33 inserts the diopter correction lens into the optical path via the diopter correction lens driving unit 8 when the diopter correction determination unit 31 determines that the diopter correction lens needs to be inserted. The driving control unit 33 pulls out the diopter correction lens from the optical path via the diopter correction lens driving unit 8 after imaging is completed, for example. In other words, the driving control unit 33 corresponds to an example of a control unit for controlling insertion and removal of the diopter correction lens into and from the optical path.

The driving control unit 33 drives the focusing lens 3 to the in-focus position determined by the in-focus position determination unit 32 after the diopter correction lens is inserted into the optical path, for example. More specifically, the driving control unit 33 serving as an example of the control unit inserts the diopter correction lens into the optical path after the driving unit drives the focusing lens 3 to the position determined by the position determination unit. Timing at which the focusing lens 3 is driven may be the same time the diopter correction lens is inserted into the optical path. Alternatively, the focusing lens 3 may be driven after the diopter correction lens is inserted into the optical path.

In a manual focusing mode, the driving control unit 33 controls the focusing lens driving unit 6 and the focus index shift driving unit 15 so that the position of the focusing lens 3 on the optical axis L1 and the position of the focus index projection unit 11 on the optical axis L2 move in synchronization according to the input of an operation of the operation input unit 28. In an automatic focusing mode, the driving control unit 33 controls the focusing lens driving unit 6 and the focus index shift driving unit 15 based on a detection result of the in-focus state detection unit 29.

The operation input unit 28 includes an imaging switch (not illustrated). When the imaging switch is pressed and the fundus camera enters an imaging state, the system control unit 17 controls the focus index insertion/removal driving unit 16, to retract the focus index projection unit 11 from the optical axis L2. Further, the system control unit 17 controls light amount adjustment, lighting, and extinction of the infrared LED 21 serving as observation light, and light amount adjustment, lighting, and extinction of the flash light source 19 serving as imaging light.

An imaging unit 27 includes the image sensor 5, the A/D conversion element 22, the memory 23, a monitor 25, and an imaging unit control unit 26, for example. The monitor 25 displays an infrared observation image and visible imaging image, which have been captured by the image sensor 5, for example. Further, the imaging unit 27 is detachably attached to the housing of the fundus camera optical unit, for example, by a mount unit (not illustrated).

An example of an operation of the ophthalmologic apparatus (e.g., the fundus camera) according to the present exemplary embodiment will be described below.

Light emitted from the infrared LED 21 is condensed by the condenser lens 20, to pass through the dichroic mirror 14, and is then restricted in a ring shape by the ring diaphragm 13. The light, which has been restricted by the ring diaphragm 13, forms an image of the ring diaphragm 13 on the perforated mirror 9 once via the lens 12 and the lens 10, and forms an image of the ring diaphragm 13 again in the vicinity of the pupil Ep of the subject's eye E by the objective lens 1 after being reflected in a direction of the optical axis L1 by the perforated mirror 9, to illuminate the fundus Er of the subject's eye E.

A light flux, which has been reflected and scattered from the fundus Er illuminated with the light from the infrared LED 21 for emitting the stationary light, is imaged after exiting from the pupil Ep of the subject's eye E and reaching the image sensor 5 via the objective lens 1, the imaging diaphragm 2, the focusing lens 3, and the imaging lens 4. After an output of the image sensor 5 is converted into a digital signal by the A/D conversion element 22, a fundus observation image is displayed on the monitor 25 via the imaging unit control unit 26.

The operator observes the fundus observation image displayed on the monitor 25, and uses an operation lever (not illustrated), to align the subject's eye E and the fundus camera optical unit.

Figure 3:
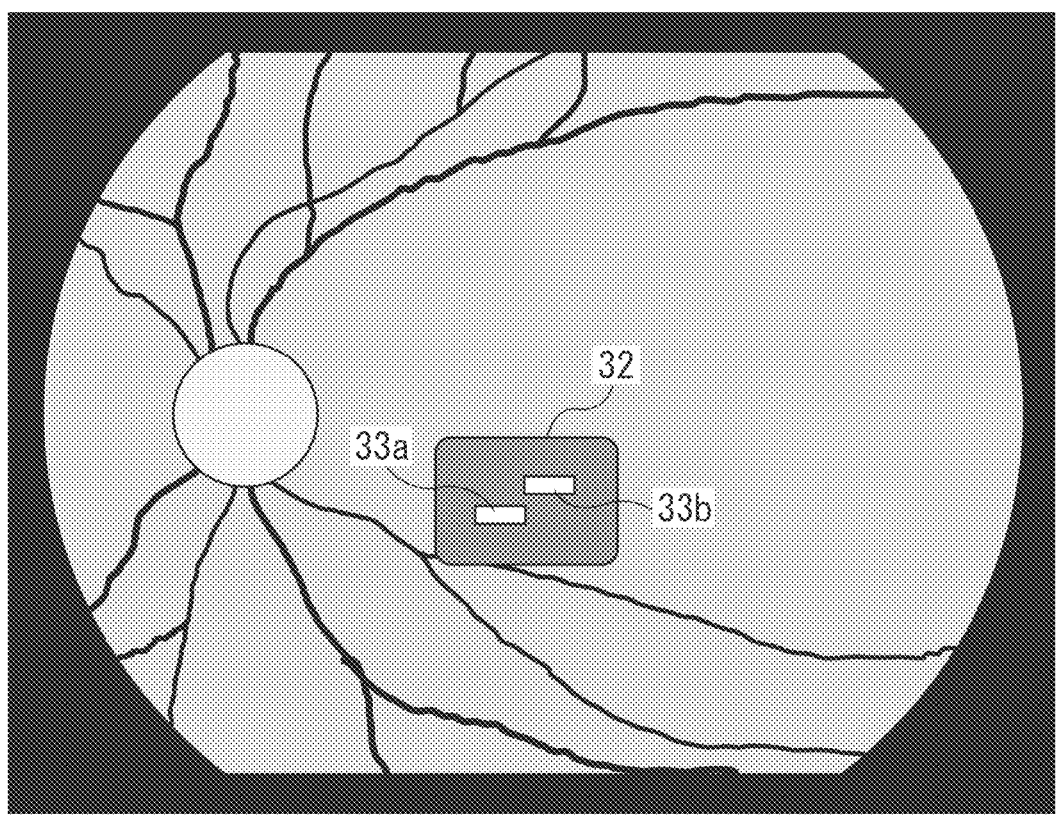
FIG. 3 illustrates an example of a fundus observation image displayed on a monitor 25 and focus index images.

FIG. 3 illustrates an example of the fundus observation image displayed on the monitor 25. During the observation, the focus index projection unit 11 is inserted onto the optical axis L2 so that the focus index mask 11c in the focus index projection unit 11 and the focus index images 33a and 33b are observed in a state where they are superimposed on the fundus observation image. More specifically, the image sensor 5 images return light, which has passed through the focusing lens 3 from the subject's eye E, of the divided indexes projected onto the subject's eye E by the focus index projection unit 11, to obtain the focus index images 33a and 33b. An output of the image sensor 5 is displayed on the monitor 25. In other words, the image sensor 5 corresponds to an example of an acquisition unit for acquiring the plurality of index images based on the return light, obtained via the focusing lens 3 from the subject's eye E, of the divided indexes.

Figure 4A:
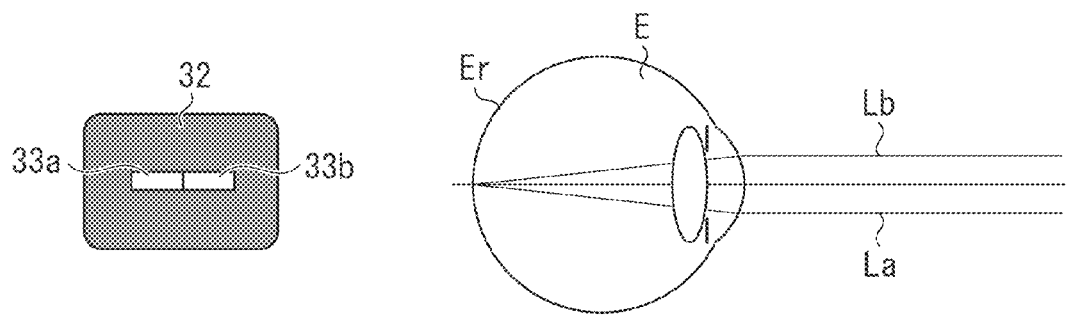
FIGS. 4A, 4B, and 4C respectively illustrate examples of focus indexes.
Figure 4B:
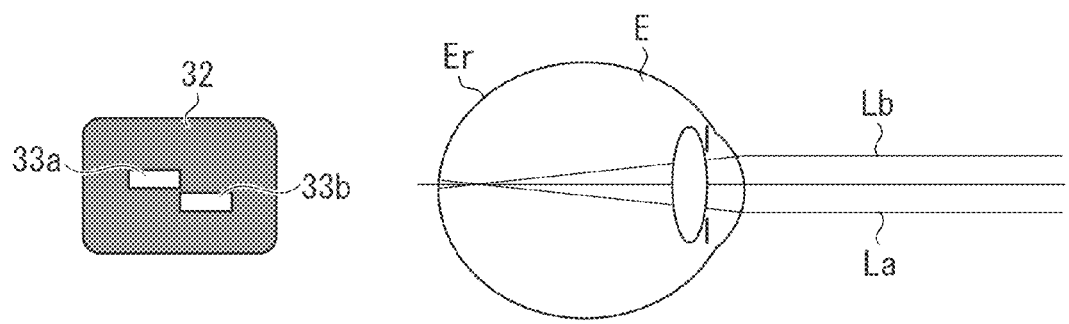
Figure 4C:
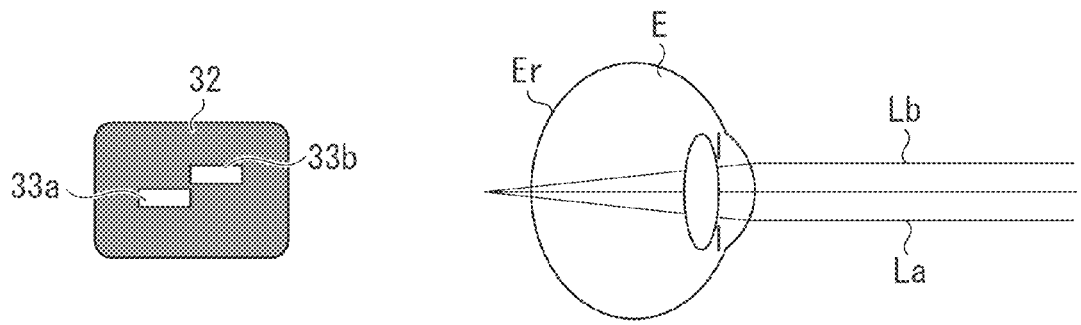

FIGS. 4A to 4C each illustrate an example of the focus indexes. FIG. 4A illustrates a case where the fundus Er of the subject's eye E and the focus index (the focus index projection unit 11) are in an optically conjugate positional relationship. Since the fundus Er and the focus indexes are optically conjugate with each other, two separated focus index light fluxes La and Lb respectively become the focus index images 33a and 33b on the fundus Er due to a rectangular opening of the focus index, to line up.

FIG. 4B illustrates a case where the subject's eye E is myopic. Since the fundus Er and the focus indexes are not optically conjugate with each other, the focus index light fluxes La and Lb are shifted from each other in a vertical direction when they respectively become the focus index images 33a and 33b on the fundus Er.

On the other hand, FIG. 4C illustrates a case where the subject's eye E is hyperopic. Also in this case, the fundus Er and the focus indexes are not conjugate with each other. Thus, the focus index light fluxes La and Lb are shifted from each other in the vertical direction when they respectively become the focus index images 33a and 33b. However, the focus index light fluxes La and Lb are vertically shifted from each other in an opposite positional relationship to that when the subject's eye E is myopic. At this time, the focusing lens 3 is driven in synchronization with the focus index projection unit 11 so that the focus index and the image sensor 5 are optically conjugate with each other. When the focus index images 33a and 33b line up, and the fundus Er and the focus index are optically conjugate with each other, therefore, the fundus Er and the image sensor 5 are also in an optically conjugate relationship. Thus, an observation image, which has been focused on the fundus Er, can be obtained.

A focus control method performed when a focusing mode switching unit (not illustrated) selects the automatic focusing mode will be described below.

In the present exemplary embodiment, automatic focusing is performed using the focus indexes projected on the fundus Er. When the automatic focusing is started, the in-focus state detection unit 29 in the present exemplary embodiment calculates respective positions in the vertical direction of the focus index images 33a and 33b, which are separated into left and right, of the focus index projected onto the fundus Er (see FIG. 3). A method for calculating the position includes a method for detecting a luminance value of the focus index images and calculating its center of gravity, for example. Then, a positional relationship between the left and right focus index images 33a and 33b and an amount of shift therebetween are calculated with respect to the calculated positions of the focus index images 33a and 33b, and are used as a focus state. Therefore, the automatic focusing in the present exemplary embodiment is started from a state where the focus index projection unit 11 is inserted onto the optical axis L2 and the convex lens 7a and the concave lens 7b are not inserted into the diopter correction unit 7 on the optical axis L1, i.e., the focus indexes can be observed.

Figure 5:
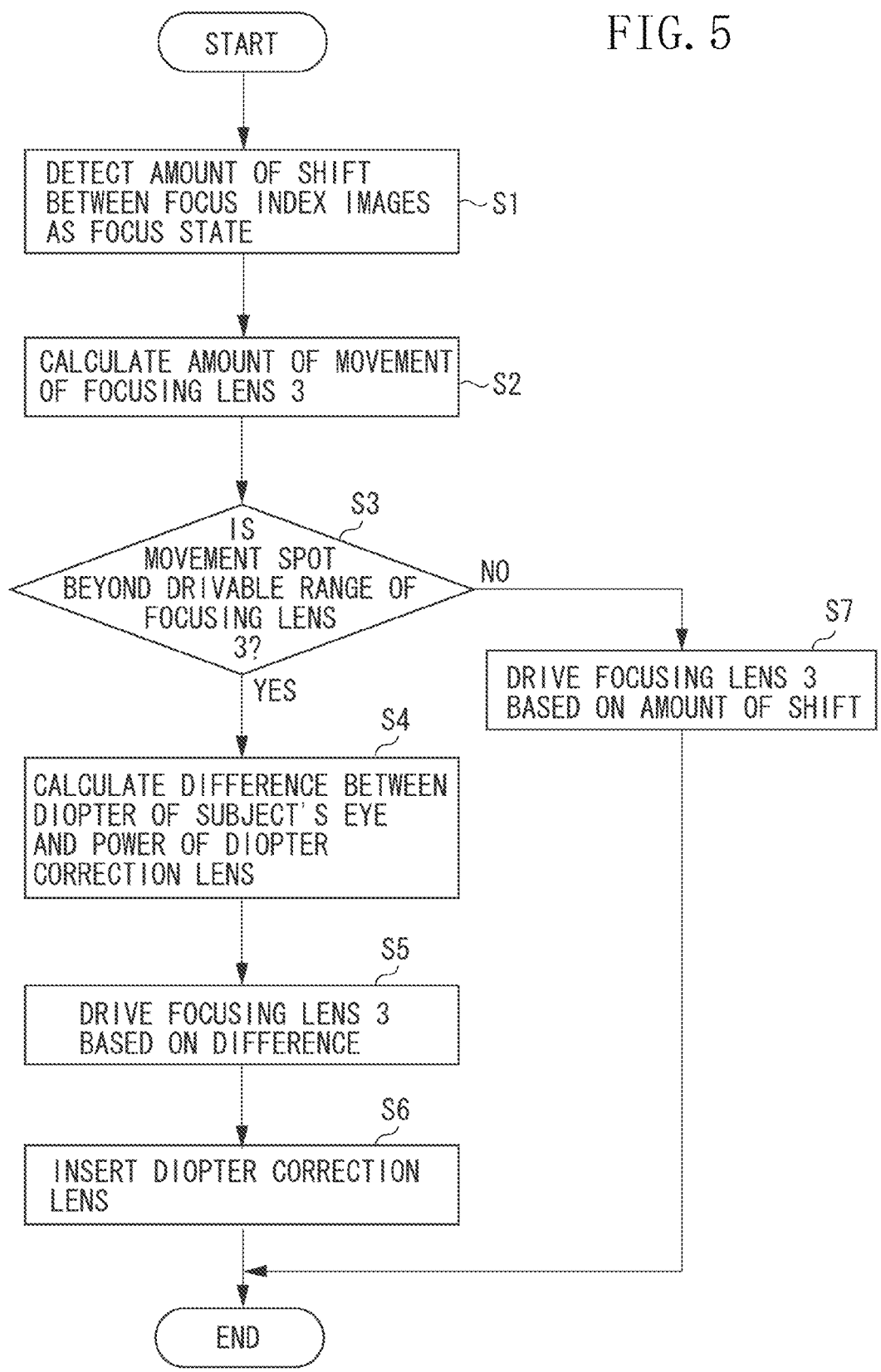
FIG. 5 is a flowchart illustrating an example of an automatic focusing operation.

FIG. 5 is a flowchart illustrating an example of an operation of the automatic focusing. An example of the operation of the automatic focusing will be described in detail with reference to FIG. 5.

If an instruction to start the automatic focusing is issued in response to completion of alignment between the subject's eye E and the fundus camera optical unit, for example, the processing proceeds to step S1. In step S1, the in-focus state detection unit 29 detects the amount of shift between the focus index images 33a and 33b as a focus state from the output of the A/D conversion element 22 stored in the memory 23. Step S1 corresponds to an example of a detection process for detecting the focus state where the diopter correction lens is not inserted into the optical path connecting the subject's eye E and the imaging unit.

In step S2, the movement amount calculation unit 30 calculates an amount of movement between the focus index projection unit 11 and the focusing lens 3 until the focus index images 33a and 33b line up from the detected focus state. More specifically, the movement amount calculation unit 30 converts the amount of shift between the focus index images 33a and 33b into the amount of movement. The amount of shift between the focus index images 33a and 33b and the amount of movement of the focusing lens 3 may preferably be associated with each other and stored as a table in the memory. Alternatively, an equation for converting the amount of shift into the amount of movement may previously be stored as a table in the memory, to calculate the amount of movement using the conversion equation.

In step S3, the diopter correction determination unit 31 detects a current position of the focusing lens 3 on the optical axis L1, and determines whether a movement spot by the amount of movement, which has been calculated by the movement amount calculation unit 30, from a position where the focusing lens 3 is stopped is beyond a drivable range of the focusing lens 3. In other words, the diopter correction determination unit 31 determines whether the focusing lens 3 can be focused on the fundus Er of the subject's eye E without inserting the diopter correction lens. The diopter correction determination unit 31 compares the drivable range of the focusing lens 3, which is stored in the memory, with the movement spot, to determine whether the diopter correction lens is to be inserted into the optical path, for example.

If it is determined that the movement spot is within the drivable range of the focusing lens 3, i.e., the focusing lens 3 can be focused (NO in step S3), then in step S7, the driving control unit 33 moves the focus index projection unit 11 and the focusing lens 3 by a predetermined distance, which has been obtained in step S2, to complete the focusing.

On the other hand, if it is determined that the movement spot is beyond the drivable range of the focusing lens 3, i.e., the focusing lens 3 cannot be focused (YES in step S3), the subject's eye E is highly myopic or highly hyperopic, for example. Thus, the diopter correction determination unit 31 determines whether the subject's eye E is myopic or hyperopic from a vertical positional relationship between the focus index images 33a and 33b, which are separated into left and right, to determine which of the convex lens 7a and the concave lens 7b is inserted as the diopter correction lens. In other words, the diopter correction determination unit 31 determines which of the diopter correction lens for hyperopia and the diopter correction lens for miopia is to be inserted based on the in-focus state where the diopter correction lens is not inserted. If the amount of shift between the focus index images 33a and 33b is not an absolute value and is a value representing the vertical positional relationship, the positional relationship between the focus index images 33a and 33b need not be used.

Figure 6A:
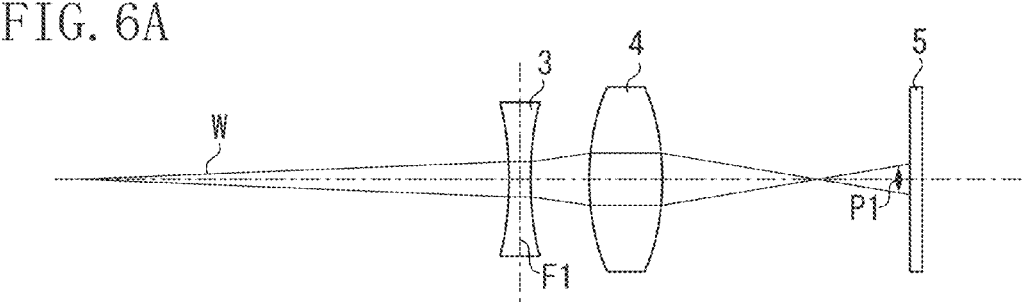
FIGS. 6A, 6B, 6C, and 6D respectively illustrate examples of determination of an in-focus position in diopter correction.

FIG. 6A illustrates a part of the observation imaging optical system when the subject's eye E is highly myopic and it is determined that the focusing lens 3 cannot be focused in a state where the diopter correction lens is not inserted. A focus index light flux W, which has been reflected from the fundus Er of the subject's eye E to pass through the objective lens 1 and the imaging diaphragm 2, reaches the image sensor 5 via the focusing lens 3 and the imaging lens 4. However, the subject's eye E is highly myopic so that the focus index images 33a and 33b cannot line up on an imaging plane. In the subject's eye E that is highly myopic, the concave lens 7b is inserted as the diopter correction lens. If the diopter correction lens is inserted, however, an optical relationship between the observation imaging optical system and the focus index projection optical system is broken so that a focus detection unit using the focus indexes cannot be used.

Figure 6B:
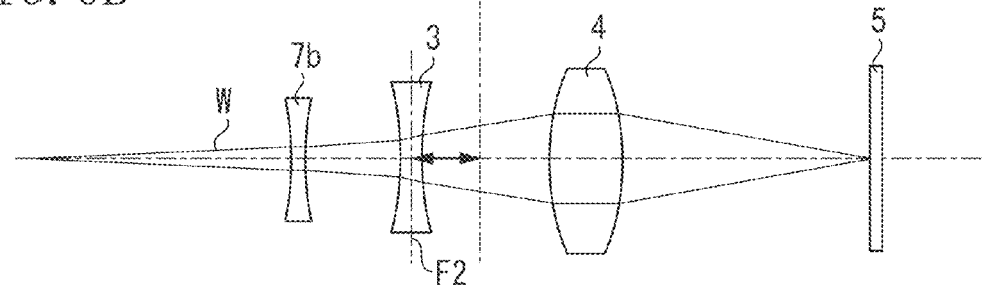

The system control unit 17 determines the in-focus position F2 when the concave lens 7b is inserted as the diopter correction lens based on an amount of shift P1 between the focus index images 33a and 33b, which have been calculated by the in-focus state detection unit 29, and a position F1 of the focusing lens 3, in the state illustrated in FIG. 6A where the diopter correction lens is not inserted (see FIG. 6B).

More specifically, the in-focus position determination unit 32 calculates the diopter of the subject's eye E from the amount of shift between the focus index images 33a and 33b and the position of the focusing lens 3. In step S4, the in-focus position determination unit 32 calculates a difference between the calculated diopter and power (correctable diopter: refractive power) of the diopter correction lens to be inserted into the optical path.

The in-focus position determination unit 32 calculates a position of the focusing lens 3 (the position F2 illustrated in FIG. 6B) on the optical path to compensate for the difference. In step S5, the in-focus position determination unit 32 drives the focusing lens 3 to the calculated position. In other words, the in-focus position determination unit 32 determines the position of the focusing lens 3 on the optical path in a state where the diopter correction lens is inserted, based on the diopter of the subject's eye E and the refractive power of the focus correction lens, which are obtained based on the in-focus state where the diopter correction lens is not inserted. More specifically, the in-focus position determination unit 32 determines the position of the focusing lens 3 on the optical path in a state where the diopter correction lens is inserted based on the difference between the diopter of the subject's eye E and the refractive power of the diopter correction lens. Step S5 corresponds to an example of a determination process for determining a position of the focusing lens 3 on the optical path in a state where the diopter correction lens is inserted into the optical path, based on the in-focus state detected in the detection process.

In step S6, the diopter correction determination unit 31 then inserts the diopter correction lens corresponding to the diopter of the subject's eye E into the optical path, to complete the focusing.

FIG. 6B illustrates the observation imaging optical system at this time. The focus index projection unit 11 is retracted from the optical axis L2 in response to the insertion of the diopter correction lens. An execution order of steps S5 and S6 is not limited to that illustrated in FIG. 5. Step S6 may be executed prior to step S5. Alternatively, steps S5 and S6 may be simultaneously executed.

Figure 6C:
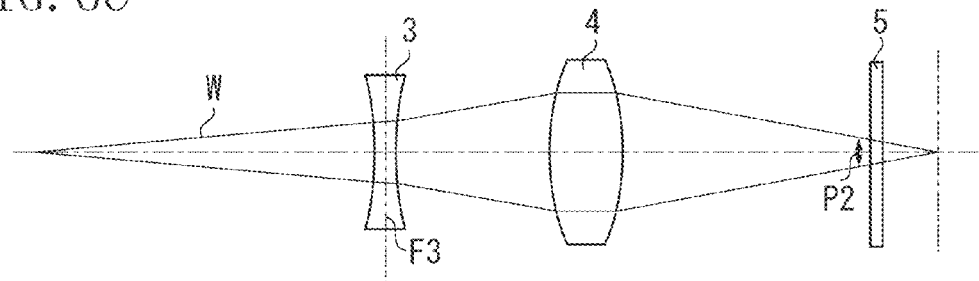
Figure 6D:
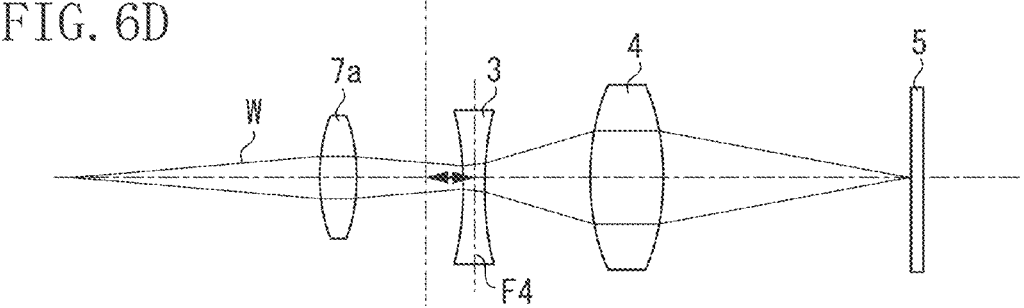

On the other hand, FIG. 6C illustrates a case where the subject's eye E is highly hyperopic. At this time, the focus index light flux W is imaged in an opposite vertical positional relationship to that when the subject's eye E is highly myopic on the imaging plane. Thus, the subject's eye E can be determined to be highly hyperopic. If the subject's eye E is highly myopic, the diopter is corrected with the convex lens 7a. However, the system control unit 17 determines an in-focus position F4 when the convex lens 7a is inserted as the diopter correction lens based on an amount of shift P2 between the focus index images 33a and 33b and a position F3 of the focusing lens 3 before inserting the convex lens 7a as the diopter correction lens. Then, the system control unit 17 drives the diopter correction lens driving unit 8 and the focusing lens driving unit 6, and inserts the diopter correction lens and moves the focusing lens 3, to complete the focusing. FIG. 6D illustrates the observation imaging optical system at this time. The focus index projection unit 11 is retracted from the optical axis L2 in response to the insertion of the diopter correction lens. An operation of the ophthalmologic apparatus performed in the automatic focusing is substantially similar to that in FIGS. 6A and 6B except for the type of the diopter correction lens to be inserted, and hence detailed description thereof is not repeated.

The in-focus position is thus determined before the diopter correction lens is inserted, thereby enabling focusing in the automatic focusing mode even on the highly myopic or highly hyperopic subject's eye E that requires the diopter correction lens for fundus imaging. The in-focus position need not be searched for after the diopter correction lens is inserted. Thus, the focusing can be completed more quickly, to shift to imaging. As a result, a period of time required for the automatic focusing can be prevented from being lengthened.

The less blurred and the more clear the focus index is, the higher the accuracy of calculation of the position of the focus index based on a luminance value in the automatic focusing mode becomes, and the more blurred and the less clear the focus index is, the lower the accuracy thereof becomes. Therefore, an amount of shift between the focus index images calculated based on the positions of the focus index images and the accuracy of determination of an in-focus position performed when the diopter correction lens is inserted can also change depending on the sharpness of the focus index images.

Therefore, in the automatic focusing required to insert the diopter correction lens, the focus index images 33a and 33b can desirably be observed more clearly to determine the in-focus position with higher accuracy. More specifically, the in-focus position may preferably be calculated after the focusing lens 3 is moved to a position that is as close as possible to the in-focus position. If the subject's eye E is highly myopic or highly hyperopic, an end of the drivable range of the focusing lens 3 is closest to the in-focus position. If it is determined that the diopter correction lens is inserted, the focusing lens 3 may be moved once to the end of the drivable range (a limit position in a range in which the driving unit can drive the focusing lens 3), to calculate the amount of shift between the focus index images 33a and 33b again and determine the in-focus position. More specifically, the driving control unit 33 serving as an example of the driving unit drives the focusing lens 3 to a predetermined position on the optical path if the determination unit determines that the diopter correction lens is to be inserted. Further, the in-focus position determination unit 32 serving as an example of the position determination unit determines a position of the focusing lens 3 on the optical path in a state where the diopter correction lens is inserted, based on the in-focus state where the focusing lens 3 is arranged at the predetermined position.

As another method, the diopter correction determination unit 31 may determine whether the diopter correction lens is inserted only when the focusing lens 3 reaches the end of the drivable range, and determine the in-focus position with the amount of shift between the focus index images 33*a* and 33*b* that has been calculated in this case. The diopter correction determination unit 31 serving as an example of the determination unit determines whether the diopter correction lens is to be inserted into the optical path in response to the driving of the focusing lens 3 to a predetermined position by the driving unit. In the above-mentioned example, while various types of control are performed based on the in-focus state occurring when the focusing lens 3 reaches the end of the drivable range to make the focus index images 33*a* and 33*b* clear, the present invention is not limited to this. The control may be performed when the focusing lens 3 reaches the vicinity of the drivable range.

MODIFIED EXAMPLE

Figure 7:
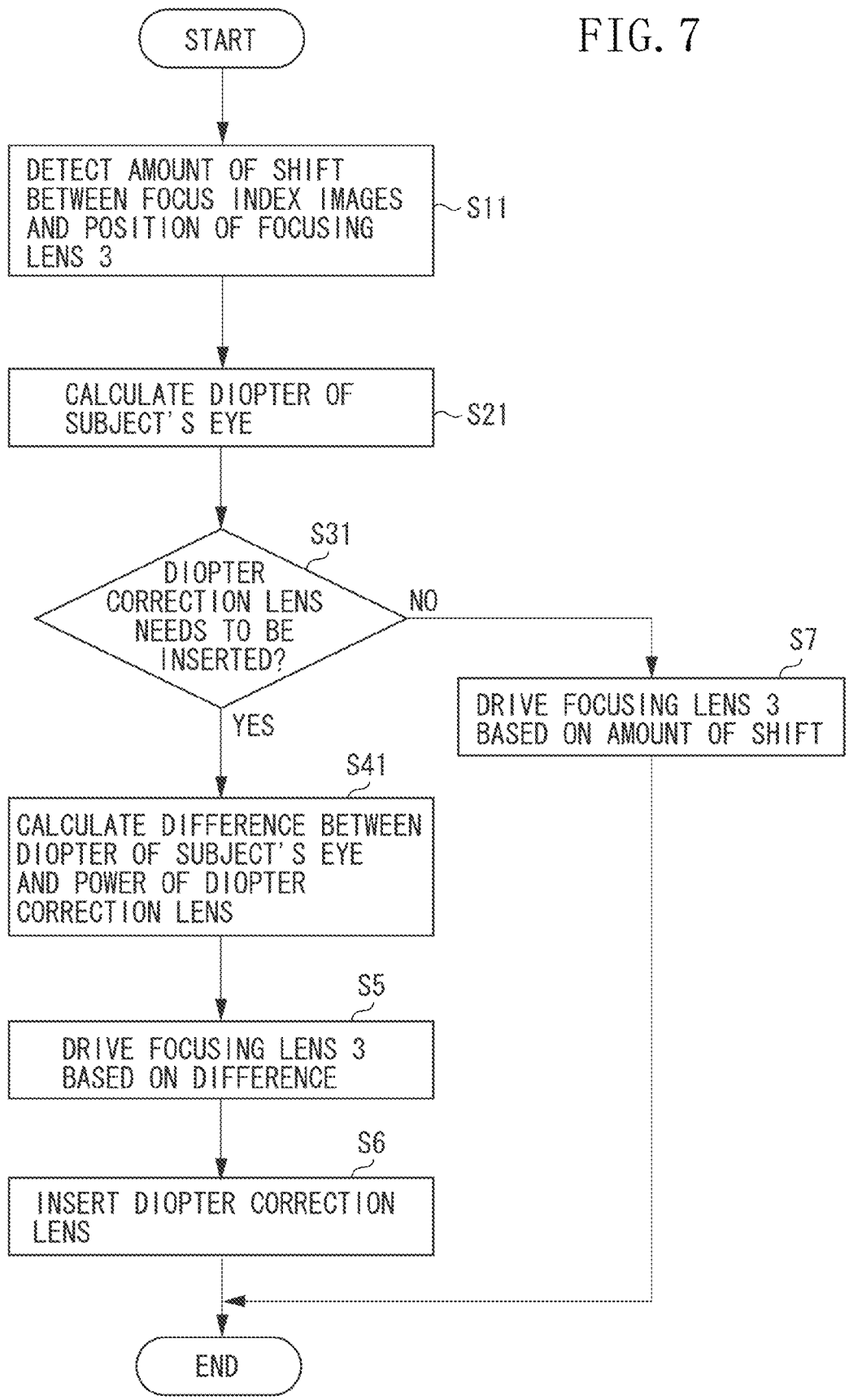
FIG. 7 is a flowchart illustrating an example of an automatic focusing operation.

A modified example of an operation of automatic focusing will be described below. In an example of the automatic focusing illustrated in FIG. 5, the amount of movement of the focusing lens 3 is calculated from the amount of shift between the focus index images 33*a* and 33*b*, and it is determined whether the diopter correction lens is to be inserted into the optical path depending on whether the calculated amount of movement is beyond the movable range. However, a method for determining whether the diopter correction lens is to be inserted is not limited to this. The determination may be performed using the diopter of the subject's eye E. The automatic focusing will be specifically described with reference to a flowchart illustrated in FIG. 7.

If an instruction to start the automatic focusing is issued, the processing proceeds to step S11. In step S11, the in-focus state detection unit 29 detects an amount of shift between the focus index images 33*a* and 33*b* from an output of the A/D conversion element 22, which has been stored in the memory 23, while detecting a position of the focusing lens 3 on the optical path.

In step S21, the in-focus position determination unit 32 calculates the diopter of the subject's eye E from the amount of shift between the focus index images 33*a* and 33*b* and the position of the focusing lens 3. In other words, the in-focus position determination unit 32 calculates the diopter of the subject's eye E based on an in-focus state where the diopter correction lens is not inserted.

In step S31, the diopter correction determination unit 31 then determines whether the focusing lens 3 can be focused on the subject's eye E having the diopter, which has been calculated in step S21, in a state where the diopter correction lens is not inserted. More specifically, the diopter correction determination unit 31 stores a range of the diopter to be coped with, which is determined by an optical design, in a storage unit such as a memory. If the diopter, which has been calculated in step S21, is not within the above-mentioned range, the in-focus state detection unit 29 determines that the diopter correction lens needs to be inserted. In other words, the diopter correction determination unit 31 acquires the diopter of the subject's eye E based on the in-focus state where the diopter correction lens is not inserted, and determines whether the diopter correction lens is inserted into the optical path based on the diopter.

If it is determined that the diopter correction lens needs to be inserted (YES in step S31), then in step S41, the in-focus position determination unit 32 calculates a difference between the diopter, which has been calculated in step S21, and a correctable diopter of the diopter correction lens to be inserted into the optical path.

Steps S5 to S7 are substantially similar to steps assigned the same reference numerals in FIG. 5, and hence detailed description thereof is not repeated.

Even if a value of the diopter itself is thus used, a similar effect to that in the above-mentioned exemplary embodiment can be obtained.

The present invention is not limited to the above-mentioned exemplary embodiments. The present invention can be implemented by various modifications and changes without departing from the spirit of the present invention.

While the fundus camera has been described as the ophthalmologic apparatus in the above-mentioned exemplary embodiments, for example, the present invention is not limited to this. The present invention may be applicable to an ophthalmologic apparatus such as a measurement apparatus or an optical coherence tomographic (OCT) apparatus.

The present invention is also implemented by performing the following processing, i.e., processing for supplying software (a program) for implementing the function of the above-mentioned exemplary embodiments to a system or an apparatus via a network or various recording media and causing a computer (or a central processing unit (CPU) or a microprocessing unit (MPU)) in the system or the apparatus to read out and execute the program.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-247356 filed Nov. 9, 2012, which is hereby incorporated by reference herein in its entirety.

What is claimed is:

1. An ophthalmologic apparatus comprising:
   a focusing lens provided in an optical path connecting a subject's eye and an imaging unit;
   a diopter correction lens configured to be insertable into and removable from the optical path; and
   a position determination unit configured to determine a position of the focusing lens in the optical path in a state where the diopter correction lens is inserted into the optical path, based on a focus state between the imaging unit and a fundus of the subject's eye where the diopter correction lens is not inserted into the optical path.

2. The ophthalmologic apparatus according to claim 1, further comprising:
   a control unit configured to control insertion and removal of the diopter correction lens into and from the optical path, and
   a driving unit configured to drive the focusing lens,
   wherein the control unit inserts the diopter correction lens into the optical path after the driving unit drives the focusing lens to the position determined by the position determination unit.

3. The ophthalmologic apparatus according to claim 2, further comprising a determination unit configured to determine whether the diopter correction lens is to be inserted into the optical path based on the in-focus state where the diopter correction lens is not inserted,
    wherein the position determination unit determines the position of the focusing lens on the optical path when the determination unit determines that the diopter correction lens is to be inserted.

4. The ophthalmologic apparatus according to claim 3, wherein
    the driving unit drives the focusing lens to a predetermined position on the optical path when the determination unit determines that the diopter correction lens is to be inserted, and
    the position determination unit determines the position of the focusing lens on the optical path in a state where the diopter correction lens is inserted, based on an in-focus state where the focusing lens is arranged in the predetermined position.

5. The ophthalmologic apparatus according to claim 4, wherein the predetermined position is a limit position in a range in which the driving unit can drive the focusing lens.

6. The ophthalmologic apparatus according to claim 3, wherein the determination unit determines whether the diopter correction lens is to be inserted into the optical path in response to the driving of the focusing lens to a predetermined position by the driving unit.

7. The ophthalmologic apparatus according to claim 3, wherein the determination unit acquires an amount of driving of the focusing lens required for focusing based on the in-focus state where the diopter correction lens is not inserted, and determines that the diopter correction lens is to be inserted into the optical path if the focusing lens is beyond a drivable range when driven by the amount of driving.

8. The ophthalmologic apparatus according to claim 3, wherein the determination unit acquires the diopter of the subject's eye based on the in-focus state where the diopter correction lens is not inserted, and determines whether the diopter correction lens is to be inserted into the optical path based on the diopter.

9. The ophthalmologic apparatus according to claim 8, wherein
    the diopter correction lens includes a diopter correction lens for hyperopia and a diopter correction lens for miopia, and
    the determination unit determines which of the diopter correction lens for hyperopia and the diopter correction lens for miopia is to be inserted, based on the in-focus state where the diopter correction lens is not inserted.

10. The ophthalmologic apparatus according to claim 1, further comprising:
    a projection unit configured to project divided indexes onto the subject's eye, and
    an acquisition unit configured to acquire a plurality of index images based on return light of the divided indexes obtained via the focusing lens from the subject's eye,
    wherein the position determination unit determines a position of the focusing lens on the optical path in a state where the diopter correction lens is inserted, based on the in-focus state where the diopter correction lens is not inserted, which is obtained from the plurality of index images.

11. The ophthalmologic apparatus according to claim 10, wherein the position determination unit determines the position of the focusing lens on the optical path in a state where the diopter correction lens is inserted, based on the in-focus state where the diopter correction lens is not inserted, which is obtained from an amount of shift between the plurality of target images.

12. The ophthalmologic apparatus according to claim 1, wherein the position determination unit determines the position of the focusing lens on the optical path in a state where the diopter correction lens is inserted, based on the in-focus state where the diopter correction lens is not inserted and the position of the focusing lens in the optical path.

13. The ophthalmologic apparatus according to claim 1, wherein the position determination unit determines the position of the focusing lens on the optical path in a state where the diopter correction lens is inserted based on the diopter of the subject's eye obtained based on the in-focus state where the diopter correction lens is not inserted and refractive power of the diopter correction lens.

14. The ophthalmologic apparatus according to claim 13, wherein the position determination unit determines the position of the focusing lens on the optical path in a state where the diopter correction lens is inserted, based on a difference between the diopter of the subject's eye and the refractive power of the diopter correction lens.

15. The ophthalmologic apparatus according to claim 1, wherein the position of the focusing lens on the optical path in a state where the diopter correction lens is inserted is an in-focus position in a state where the diopter correction lens is inserted.

16. A control method comprising:
    arranging a focusing lens in an optical path connecting a subject's eye and an imaging unit;
    providing a diopter correction lens configured to be insertable into and removable from the optical path;
    detecting a focus state where the diopter correction lens is not inserted into the optical path connecting a subject's eye and an imaging unit; and
    determining a position of the focusing lens in the optical path in a state where the diopter correction lens is inserted into the optical path, based on the detected focus state between the imaging unit and a fundus of the subject's eye where the diopter correction lens is not inserted into the optical path.

* * * * *